United States Patent [19]

Sankey et al.

[11] Patent Number: 5,266,587
[45] Date of Patent: Nov. 30, 1993

[54] PEROXYCARBOXYLIC ACIDS AND COMPOSITIONS CONTAINING SUCH

[75] Inventors: John P. Sankey; A. Pryce James, both of Widnes, United Kingdom

[73] Assignee: Interox Chemicals Limited, London, England

[21] Appl. No.: 752,669

[22] PCT Filed: Dec. 20, 1990

[86] PCT No.: PCT/GB90/01988
§ 371 Date: Aug. 23, 1991
§ 102(e) Date: Aug. 23, 1991

[87] PCT Pub. No.: WO91/09843
PCT Pub. Date: Jul. 11, 1991

[30] Foreign Application Priority Data

Dec. 23, 1989 [GB] United Kingdom ............... 8929186
Dec. 4, 1990 [GB] United Kingdom ............... 9026280

[51] Int. Cl.$^5$ ........................................ C07D 209/48
[52] U.S. Cl. .................... 514/417; 252/102; 8/111; 422/28; 548/473; 548/480
[58] Field of Search ............... 548/480, 473; 252/188.1, 102; 8/111; 514/417; 422/28

[56] References Cited

U.S. PATENT DOCUMENTS 3,143,562 8/1964 Silbert et al. .................. 260/465
3,180,886 4/1965 Silbert et al. .................. 260/465

FOREIGN PATENT DOCUMENTS 0325288 7/1989 European Pat. Off. .
0325289 7/1989 European Pat. Off. .

Primary Examiner—Joseph Paul Brust
Assistant Examiner—Jacqueline Haley
Attorney, Agent, or Firm—Larson and Taylor

[57] ABSTRACT

The invention provides a new sub-class or organic peroxyacids comprising N-alkyl substituted peroxy-trimellitimide of formula (I) in which R=hydrogen or linear or branched alkyl, which demonstrates an excellent combination of safe-handling and bleach performance rendering the sub-class particularly suitable for use as bleach and/or disinfectant in various bleach, bleach additive or washing compositions. Effective bleaching peroxyacids include those in which R=n propyl, iso-propyl, n butyl, sec-butyl, n pentyl and n heptyl. The invention also comprises processes for making the peroxyacids, compositions containing them and processes for washing and/or bleaching and/or disinfecting employing the invention peroxyacids or compositions containing them.

17 Claims, No Drawings

PEROXYCARBOXYLIC ACIDS AND COMPOSITIONS CONTAINING SUCH

The present invention relates to peroxycarboxylic acids and more particularly to peroxycarboxylic acids which contain within their structure an imido linkage, to the preparation of such percarboxylic acids and to their use in bleaching compositions and in washing compositions.

Organic peroxycarboxylic acids, sometimes alternatively called percarboxylic acids or organic peracids, as a class, are potentially very useful oxidising agents as a result of their high redox potential which enables them to bleach very effectively a wide range of stains that mark domestic laundry or non-absorbent surfaces in the home and to be very useful disinfectants or sanitizers on account of their biocidal activity against a broad spectrum of pathogenic micro-organisms. Self-evidently, some percarboxylic acids are more effective than others in such activities, but the relative efficacy of the percompounds is only one key factor in determining the potential usefulness of such percompounds because they vary also in a second key area, which is the physical characteristics of the percompounds and specifically their sensitivity to impact, pressure or thermal shock and their propensity to decompose during storage, either by themselves or in contact with other components of washing or bleaching compositions. Variation in respect of both factors occurs as a direct result of what else is present in the percarboxylic acid molecule and the structural relationship of for example the various substituents to the percarboxylic acid group and to each other.

It is easy for the skilled person in this field to set out a number of desiderata; i.e. criteria that a peroxyacid ought to satisfy, in order to be considered an effective and acceptable bleaching component. If the peroxyacid is being produced in situ, then the criterion of overwhelming importance is its performance, i.e. to what extent does it wash and bleach, but if it is being employed as a preformed compound, then a number of other criteria assume similar importance to its performance, including in particular whether it enjoys sufficient resistance to impact, friction, pressure and thermal shocks to enable the material to be formulated, and handled and transported, both before and after formulation, and also enjoys an acceptably long shelf-storage life, i.e. successful, safe and stable.

The impression may have been fostered that all peroxyacids are similar, as a result of the inclusion of general formulae for peracids in many patent specifications, e.g. U.S. Pat. No. 4,259,201 of HO—O—(-CO)—R—Y which appear to equate aliphatic and aromatic peroxyacids and a wide range of substituents. To a limited extent such an impression is justifiable, in that they do share, in general, a capability of bleaching domestic stains at lower molar amounts and at lower temperatures than hydrogen peroxide from which they are usually derived, and they can suffer from a tendency to decompose, either induced by shocks or during storage or interaction with other chemicals or material surfaces. However, the various sub-classes of peroxyacids show considerable variation in the extent to which they enjoy enhanced bleaching properties or suffer from the tendency to decompose by shock and/or in storage.

One of the sub-classes of peroxyacids tested in the course of the present investigations comprised aromatic compounds containing within their structure an imide link. A number of peroxyacids in that sub-class have been described by Ausimont Spa as bleaching agents in EP-A-0 325 289, published in August 1989, in which the imido nitrogen atom is substituted by an alkylene-peroxycarboxylic acid group. However, the peroxyacid that performed best in Ausimont's washing trials, phthalimido-peracetic acid, was found by the present investigators, amongst other things, to suffer from rather poor resistance to impact, even when desensitised by dilution with its own weight of an effective inert diluent, sodium sulphate, i.e. was relatively unsafe to handle. The bleach that performed next best in the Ausimont tests, phthalimido-perpropionic acid was found to have lost nearly half its peroxyacid activity within 4 weeks storage at 32° C., i.e. was relatively unstable. Thus, the Ausimont specification did not offer the investigators a clear teaching as to how to select safe and stable peroxyacid bleaches.

It remained an objective of the instant investigations to locate alternative peroxyacid bleaches which not only could demonstrate acceptable bleaching performance but could also meet the other requirements for practical use, namely safe handling and peroxyacid stability.

Subsequent to the priority date claimed for the instant application, two further patent applications were published which disclosed other aromatic imidoperoxyalkanoic acids, viz EP-A-0 349 940 to Hoescht and WO 90/07501 to Interox Chemicals, but neither of those applications described any of the novel selection of peroxyacids described hereinafter.

According to the present invention there is provided an organic peroxyacid which satisfies general formula (1):

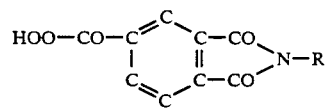

in which R represents hydrogen or a low molecular weight alkyl group containing up to 8 linear carbon atoms.

The alkyl group, R, can be linear or branched, and normally contains from 1 to 10 carbon atoms. Side chains, if present, are normally methyl, ethyl or propyl. It will be understood that whilst all the invention peracids are good at stain removal, the nature of R influences to a noticeable extent the balance in effectiveness of the invention peracids at removing various classes of stains. For removal of stains which are classified as hydrophilic, such as wine, juices or tea, it is preferable to select R from range A, which comprises hydrogen and the somewhat lower weight alkyl group, such as containing up to 5 carbons, including methyl, ethyl and propyl, iso-propyl and sec and iso-butyl. For removal biased towards more hydrophobic stains, such as grass, polish or clay stains, it is preferable to employ an overlapping, but somewhat higher range B of groups for R, such as groups containing from 3 to 8 linear carbons including iso or sec-butyl, n-pentyl, iso-pentyl, n-heptyl and trimethyl hexyl. Peracids containing an R group common to both ranges self-evidently are advantageous. Preferred ranges of the invention peroxyacids which achieve a good balanced performance are those in which R=linear C4 to C6 and R=branched C3 to C5. In a further preferred set of peroxycompounds, R is selected such that the number of linear carbon atoms in the only or the longest chain is 3, 5 or 7, though the total number of carbons in R may be even if R is branched.

A mixture of invention peracids can be employed, for example including a representative compound in which R is according to each of ranges A and B specified above.

Although the formula above is given in respect of compounds containing a single peroxytrimellitimido group, it will also be recognised that corresponding peroxyacids can be made from the reaction products of trimellitic anhydride and alkyamines that contain more than one amine group, such as alpha-omega alkylene diamines. The resultant peroxyacids accordingly can contain a corresponding number of peroxycarboxylic acid groups per molecule.

The present invention includes compounds containing a plurality of peroxytrimellitimido groups per molecule and enjoy a similar hydrophobic/hydrophilic balance to the monoperoxytrimellitimido acids identified above.

When considering selection of combinations of the various substituents in peroxyacids, it is of practical value to pay attention to the melting point of purified peroxyacid. As a general guidance, and within each sub-class of organic peroxyacids, including the sub-class comprising one aspect of the present invention, it has been found to be more desirable to select those peroxyacids which have the higher or highest apparent melting points, such as above about 70° C. For many peroxyacids, this temperature more probably represents the onset of self-accelerating decomposition rather than a simple melting point Accordingly, a preferred range of invention peracids comprises compounds in which R is hydrogen, or C1 to C3, or if C4 or larger contains an odd number of carbon atoms in the only or longest chain.

From one point of view, peroxytrimellitimide represents an excellent choice. From the viewpoint of effectiveness as a bleach, peroxytrimellitimides in which R=propyl, iso-propyl, butyl, isobutyl, pentyl or hexyl each represent an excellent choice. Taking into account all the factors identified herein, the peroxytrimellitimide which has demonstrated the best combination of properties to act as a bleach is that in which R=sec-butyl.

The invention peroxycarboxylic acids can be made by reaction between the corresponding carboxylic acid and hydrogen peroxide in a strong mineral acid or organic acid reaction medium at a reaction temperature of below about 50° C., preferably from 5° to 30° C. maintained until peroxyacid product precipitates out of solution, and thereafter separating the product from the reaction medium. Most conveniently, a product having excellent characteristics can be obtained employing a reaction at about ambient temperature, i.e. around 20° to 25° C.

It is rather surprising that a sulphuric acid reaction medium can be employed successfully, because prior art, such as U.S. Pat. Nos. 3,143,562 and 3,180,880 to Silbert and Swern, teaches that such a medium is not applicable to the peroxidation of aromatic peroxycarboxylic acids, i.e. compounds in which the carboxylic acid is a direct substituent of an aromatic nucleus. Where sulphuric acid was suggested as the reaction medium for the peroxidation of a sulphoaromatic carboxylic acid, as in EP-A-0 124 968, to Interox Chemicals Limited, for production of a sulphoperbenzoic acid, reaction did occur to a limited extent, but reaction was rendered practicable by use of an alkanesulphonic acid. Similar reaction procedures are known for making poorly soluble aliphatic peroxyacids, and these can be applied to the manufacture of the invention peroxyacids. In effect, the processes taught in such prior publications as Siegel, et al in JOC, vol 27 pp1336–42 in 1961 entitled peroxides IX. New Method for the Direct Preparation of Aromatic and Aliphatic Peroxyacids can be employed, but modified as to the carboxylic acid starting materials. Likewise, various processes described for the production of aliphatic peroxyacids in each of U.S. Pat. No. 2,813,896 (Krimm) U.S. Pat. No. 4,119,660 (Hutchins), U.S. Pat. No. 4,172,086 (Berkowitz), U.S. Pat. No. 4,233,235 (Camden) and U.S. Pat. No. 4,337,213 Marynowski.

Thus, when an organic acid reaction medium for the peroxidation reaction, is employed, it is especially suitably an organic sulphonic acid, such as specifically methane sulphonic acid, which is probably the most readily available lower alkane sulphonic acid. When an inorganic mineral acid reaction medium is employed, it is most preferably sulphuric acid or can alternatively be phosphoric acid. Mixtures of the strong acids, either wholly inorganic or organic and inorganic, can be employed if desired.

The carboxylic acid starting material may be introduced into the reaction vessel as a particulate solid or dissolved or slurried in at least a part of the inorganic or strong organic acid reaction medium.

It will also be recognised that where the reaction medium comprises a mineral acid, such as sulphuric acid, all or part of it can be premixed with the hydrogen peroxide to form an equilibrium mixture containing for example permonosulphuric acid that can itself perform the peroxidation reaction. Such premixing is beneficial because it separates the exothermic dilution/reaction between hydrogen peroxide and sulphuric acid from the peroxidation reaction, thereby enabling both to be controlled more readily and safely.

The attention of readers not skilled in the art of peroxygen chemistry is directed to the potentially hazardous nature of peroxidation reactions and their products, to the need to take appropriate safety precautions at all times and to control the reaction conditions so as to ensure that the reaction mixture never at any time exceeds its SADT, self accelerating decomposition temperature and to carry out any initial tests on a very small scale.

Notwithstanding the above general warning which is of particular relevance to the formation of many peroxyacids, the isolated peroxyacids of the instant invention are characterised by their generally benign properties, specifically their relatively high stability and resistance to decomposition which they combine with acceptable bleach performance.

It will be recognised that the invention peroxyacids described hereinbefore are obtainable by peroxidation of the corresponding precursor imido-containing carboxylic acids, which, if they are not readily available, can themselves be obtained by a conventional condensation between trimellitic anhydride and the appropriate amine or between trimellitimide and the appropriate chloroalkane.

Whilst the instant invention relates primarily to the peroxyacids themselves, it will be understood that it is possible to form magnesium salt derivatives of the peroxyacids by the steps of a) neutralisation using magnesium oxide or similar compounds in media rendered alkaline to above the $pK_a$ of the peroxyacid and b) recovery of the product that is permitted or induced to precipitate out. These corresponding salts share the same wash performance of the peroxyacids themselves and represent an alternative solid vehicle for the peroxyacids.

The percarboxylic acids according to the instant invention are particulate solids and they can be employed by themselves or can be incorporated as an active bleach component in bleaching or washing compositions containing a range of other ingredients, the selection and amounts of which are at the discretion of the formulator and determine the name for the compositions.

Extensive testing of the invention peroxyacids has demonstrated that they are less hazardous, as measured by the impact and/or pressure time test described herein than is diperoxydodecanedioic acid (DPDDA) a currently favoured benchmark peroxyacid, especially when R=alkyl and that in general they demonstrate comparable or better storage stability than DPDDA. Thus, all represent an advantageous replacement for DPDDA and those which enjoy the best performance offer an especially beneficial combination of properties.

For bleach or bleach additive compositions, the peroxyacid normally comprises from 1 to 80%, and often from 5 to 50%, all %s herein being w/w of the respective composition unless otherwise stated The remainder, 99 to 20%, comprises a diluent either by itself or together with a minor amount, such as up to 20% in total of optional components such as peroxygen stabilisers, surfactants, etc as indicated subsequently herein. The skilled reader will recognise that many of the diluents described herein as being suitable have hitherto been described as one or other of desensitising diluents or stabilising diluents or exotherm control agents in conjunction with named prior art organic peroxyacids such as DPDDA. Whilst the presence of such diluent compounds may have been necessary to perform that function for those prior art peroxyacids, it is a significant feature of most of the invention peroxyacids that the presence of the same diluents is optional and in practice their selection can be based upon any other desirable feature of those compounds, such as their cheapness or their advantageous washing or detergent-enhancing properties.

The diluent is often a salt selected from anhydrous or hydrated alkali or alkaline earth metal salts of halogen-free acids, and particularly of mineral acids, including salts of sulphuric, and ortho, pyro or hexa-meta phosphoric acids. Preferably, the metal is selected from sodium, potassium and magnesium and in many instances is sodium. Hydrated, partially hydrated or anhydrous sodium sulphate is often chosen in view of its widespread availability, its properties and its cost. It will be recognised, though, that use of a phosphate salt may be preferred in view of its known capabilities of acting as a detergent builder, which can complement especially an unbuilt washing composition.

Other inorganic compounds that are suitable for use as diluents include ortho and meta boric acid and alkali metal salts thereof, and especially sodium salts. Such compounds can buffer solutions of the bleach or additive composition to a pH in the immediate region of the $pK_a$ of the peroxyacid and consequently optimise bleach activity. The boric acids have also been used as exotherm control agents in compositions containing peroxyacids such as DPDDA that need to be protected against a tendency to decompose in an otherwise uncontrollable fashion if allowed to reach a quite low threshold temperature, but that property is unnecessary in conjunction with the invention peroxyacids on account of the safe nature of these selected imido peroxyacids.

Other suitable inorganic diluents include alkali metal carbonates/bicarbonates, aluminium salts of the above-identified mineral acids, and natural or synthetic aluminosilicates and clays, such as zeolites A, X and Y, often in the sodium form, or swelling clays like bentonite, or a layered silicate as described in EP-A-0 337 217. It will be clearly recognised that many of these diluents also enjoy the status of builders in washing compositions, and that each accordingly can perform its known functions such as hardness removal or peptising when employed in bleach compositions. When the bleach composition is intended as a scour, at least a proportion of the diluent and preferably at least half of the diluent comprises abrasive powdered materials, including silica, quartz, marble dust or kieselguhr.

A further and rather different class of suitable inorganic diluents comprises alkai metal or alkaline earth metal halides, especially chlorides and/or bromides and particularly sodium chloride, or sodium bromide or a mixture of the two. By employing this class of diluents as at least a part of the diluents, the composition can generate in solution during use of the composition a halide such as chlorine or bromine which can complement the bleaching/sanitising effect of the invention imido peroxyacids.

The diluent can comprise a hydrogen peroxide—developing solid persalt, or an inorganic persulphate, preferably in an amount of not more than 50% w/w of the composition. The term "persalt" herein relates primarily to alkali metal perborates, percarbonates and perphosphates, and especially the sodium salts, which generate hydrogen peroxide or the $HOO^-$ anion depending on the solution pH, in situ and includes other hydrogen peroxide adducts which can do likewise. Preferred persalts include sodium perborate monohydrate or tetrahydrate and sodium percarbonate. Persalts include adducts with urea and related compounds, adducts with certain aluminosilicates and addition compounds with alkali/alkaline earth metal sulphate/chlorides in specified ratios. It will be recognised that the use of persalts as diluent, such as in at least 10% of the composition, enables the composition to be effective throughout a range of temperatures from ambient up to about 100° C.

In one more specialised type of bleaching compositions, namely effervescent composition, which are often intended primarily for cleansing dentures, but which can also be employed for many other purposes, the diluent for the invention peroxyacids preferably contains a gas generating system and if necessary a pH regulator. Compounds that are suitable for gas generating systems and as pH regulators are well known in conjunction with existing peroxyacids, and are described in EP-A-0 133 354 in the name of Interox Chemicals Limited. The gas generating system often provides from 10 to 50% and comprises either a carbon dioxide generating combination of an alkali metal carbonate or bicarbonate with a solid water-soluble acid, and especially an organic acid selected from tartaric, citric, lactic, succinic, glutaric, maleic, fumaric and malonic acids, preferably in an equivalent mole ratio of from 1.5:1 to 1:1.5 and especially at about 1:1, or an oxygen-generating compound known as anhydrous sodium perborate, $NaBO_3$. The pH regulator often comprises 5 to 40% of the composition. To provide acidic conditions, it can comprise one or more of the aforementioned organic acids in an appropriate excess amount, or sulphamic acid or alkali metal bisulphates, and to provide alkaline conditions, it can comprise alkali metal silicates or excess carbonate/bicarbonates. Selection of the percarboxylic salt form can be advantageous in such compositions.

In the main, the foregoing diluents have been inorganic. However, the invention peroxyacids can be diluted, if desired, with a range of organic substances, including hydrocarbon waxes, alkyl C1 to C6 esters of aromatic mono or di carboxylic acids, solid starches, gelatines and dextrins.

The bleach compositions can also contain, as indicated before, minor components such as peroxyacid stabilisers. The breadth of compounds suitable for this purpose is well-known in this art. These are often organic chelating compounds that sequester metal ions in solution, particularly most transition metal ions, which would promote decomposition of any peroxygen compounds therein, and many suitable ones being classified in the literature as carboxylic acid, hydroxycarboxylic or aminocarboxylic acid complexing agents or as organic amino- or hydroxy-polyphosphonic acid complexing agents, either in acid or soluble salt forms. Representative stabilisers expressed in acid form include picolinic acid, dipicolinic acid, quinolinic acid, gluconic acid, hydroxyethylene di phosphonic acid, and any compound satisfying the general formula:

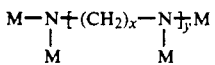

in which M represents either $-CH_2-CO_2H$ or $-CH_2-PO_3H$, x represents an integer selected from 1 to 6, and preferably is 2, and y represents an integer selected from 0, 1, 2 or 3. Within this general formula especially preferred stabilisers include ethylenediamine tetra acetic acid (EDTA), ethylenediamine tetrakis (methylenephosphonic acid) (EDTMP), and diethylenetriamine pentakis (methylenephosphonic acid) (DTPMP). A further and particularly effective stabiliser comprises cyclohexane-1,2-diamine tetrakis (methylenephosphonic acid), CDTMP. The amount of stabiliser is often up to 5% of the composition and in many instances is selected in the range of from 0.05 to 1%.

If present at all, a surfactant is present in bleaching compositions only in a small amount, such as up to about 5% and in many instances from 0.1 to 2% of the composition. It can be selected from the surfactants described subsequently herein for washing compositions.

The invention bleaching compositions will often comprise particulate mixtures, which can be stored loosely in conventional waxed boxes, or alternatively be enclosed in rupturable pouches or in porous or perforated bags or sacs through which bleaching solution can penetrate. Such mixtures can be obtained by dry blending the particulate components, or they can be aggregated using conventional agglomeration or granulation techniques, using water or a removable solvent and optionally a granulating aid hitherto described for use with an organic peroxyacid. Alternatively, by virtue of their demonstrated ability to withstand pressure, all but the least resistant invention peroxyacids can be compressed in tablets and like bodies. Accordingly, it is possible to provide peroxyacids in easy to use predetermined dosage levels for the end user.

The bleaching compositions can be used by themselves, such as in a pre-wash bleach or a post-wash rinsing stage of a multistage laundry process or in cleansing both absorbent or non-absorbent (sometimes called "hard") surfaces. They are more usually employed in conjunction with a washing composition based upon surfactants. Naturally, surfactants and optional ingredients of washing compositions can be premixed with the instant bleaching compositions to form bleach-containing washing compositions.

Washing compositions according to this further aspect of the present invention contain from 0.5 to 50% of the invention imido peroxyacids, from 1 to 90% surfactant, from 0 to 90% detergent builder, from 0 to 90% diluent and from 0 to 20% minor components. It will be recognised that the composition of the invention washing compositions range within very broad limits. Choice of the peroxyacid in acid form can be beneficial herein, in order to minimise or avoid spotting problems that can occur if excessive local concentrations of active bleach should be allowed to remain in contact with a dyed fabric for too long.

In many preferred compositions according to the present invention, one or more of the composition components are selected within the following narrower bands:

| | |
|---|---|
| imido peroxyacid | 1 to 25%, particularly 2 to 10% |
| surfactant | 2 to 40%, particularly 5 to 25% |
| builder | 1 to 60%, particularly 5 to 40% |
| diluent | 1 to 70%, particularly 5 to 50% |
| minor components | 1 to 10% in total. |

The surfactants for incorporation in solid compositions of the present invention can be selected from particulate or flaky anionic, cationic, non-ionic, zwitterionic, amphoteric and ampholytic surfactants and can be either natural soaps or synthetic. A number of suitable surfactants are described in chapter 2 of Synthetic Detergents by A Davidsohn and B. M. Milwidsky (6th edition) published in 1978 by George Godwin Ltd and John Wiley & Sons, incorporated herein by reference. Without limiting to these surfactants, representaitive sub-classes of anionic surfactants are carboxylic acid soaps, alkyl aryl sulphonates, olefin sulphonates, linear alkane sulphonates, hydroxy-alkane sulphonates, long chain and OXO alcohol sulphates, sulphated glycerides, sulphated ethers, sulpho-succinates, alkane sulphonates, phosphate esters, sucrose esters and anionic fluorosurfactants; representative classes of cationic surfactants include quaternary ammonium or quaternary pyridinium salts containing at least one hydrophobic alkyl or aralkyl group, representative classes of nonionic surfactants include condensates of a long chain alkanol or an alkyl phenol with polyethylene oxides, or condensates of long chain carboxylic acids or amines or amides with polyethylene oxide, and related compounds in which the long chain moiety is condensed with an aliphatic polyol such as sorbitol or condensation products of ethylene and propylene oxides or fatty acid alkanolamides and fatty acid amine oxides; representative classes of amphoteric/zwitterionic surfactants include sulphonium and phosphonium surfactants, optionally substituted by an anionic solubilising group. The proportion of surfactant, expressed as a fraction of all the surfactant present is often from 2/10 to 8/10ths anionic, from 0 to 6/10ths nonionic, and from 0 to 3/10ths for the other surfactants.

It will be recognised by the knowledgable reader that many of the classes of diluent described herein above for use in bleaching compositions are also called detergent builders. These include specifically alkali metal phosphates, particularly tripolyphosphate but also tetrapyrophosphate and hexametaphosphate, especially the sodium salt of each, alkali metal, preferably, sodium carbonate, alkali metal, preferably, sodium borates, and the zeolites A, X and Y and clays like bentonite. Amongst organic compounds, the chelating compounds which were described herein as peroxygen stabilisers can also function as detergent builders. Particularly preferred chelating builders include nitrilotrisodium trisacetate (NTA), EDTA, EDTMP and DTPMP. Such chelating builders can be employed in a relatively small amount as an augmenting builder and peroxygen stabiliser, such as of 1 to 10%, or in cooperative partnership of equals in conjunction with a phosphatic or zeolitic or clay builder, the weight ratio of chelating to inorganic builders often being from 4:1 to 1:4, or alternatively they can be employed as the principal builder in amounts of up to 40% such as in the range of 5 to 30% of the washing composition.

The other types of compounds that have been indicated to be suitable for use as diluents in a bleaching composition, can also be employed for the same primary purpose and secondary purpose, if any, in washing compositions, although it will be recognised that the presence of an effervescent system in washing compositions is comparatively rare. For the avoidance of doubt, persalts can be incorporated in the instant washing compositions, preferably in an amount of up to 30%, such as 1 to 20%, and sometimes in a weight ratio to the invention imido peroxyacids of from 5:1 to 1:5. A diluent commonly present in these washing compositions is sodium sulphate, often from 5 to 50%, because it also functions as a processing aid. The previously mentioned salts that enable a halogen to be generated in situ can likewise be present in the washing compositions, which can then enjoy the alternative name of sanitising compositions.

The washing compositions can contain a number of optional components, sometimes alternatively called auxiliary agents. These agents which can each individually be included include soil anti redeposition agents (SARDs), dye transfer inhibitors, optical brightening agents (OBAs), stabilisers, corrosion inhibitors, bactericides, dyes, perfumes, foam enhancers, foam inhibitors, pH regulators and absorbents. The amount for each auxiliary agent is often selected in the range of 0.02 to 0.2% for dyes and perfumes and from 0.1 to 2% for each of the other auxiliary agents. It is preferable to select auxiliary agents which are known not to interact with peroxygen compounds during storage or to coat the agent with or incorporate the agent in a known fashion within a matrix of a dispersible material such as a wax or the many other film-forming substances proposed in the literature for separating organic peroxygen compounds from co-components, e.g. in EP-B-00 27 693 to Interox Chemicals Limited. Such substances can also function as granulating aids (binders), if the invention compositions are granulated or agglomerated. Examples of suitable SARDs include carboxymethyl cellulose particularly the sodium salt, polyvinylpyrrolidone and examples of OBAs include derivatives of diaminostilbene sulphonic acid and 1,3-diaryl-2-pyrazolines and aminocoumarins.

The invention washing compositions can be dampened or dissolved in a little water for cleaning and disinfecting non-adsorbent surfaces such as walls, floors, work surfaces, vessels, baths, sinks and sanitaryware of metal, plastics, ceramics or glass, wood and rubber.

One of the main intended uses of the washing compositions is to cleanse and indeed also disinfect soiled adsorbent materials such as household laundry items or other articles made especially from cotton, rayon, flax or wool or man-made fibres such as polyesters or polyamides. The cleansing processes can be carried out at ambient temperature or at elevated temperature up to the boiling temperature of the washing solution. The more preferred washing temperature for laundry is from 30° to 60° C. In laundering, it is desirable to introduce sufficient washing composition and/or bleach additive composition to provide at least 5 ppm avox from the imido peroxyacid, and often from 10 to 50 ppm avox, ppm indicating parts per million by weight and avox indicating available oxygen. This can often be provided by the introduction of the invention washing composition selected in the range of 1 to 25 gpl, or bleach additive composition selected in the range of from 0.5 to 10 gpl, the selection taking into account the concentration of imido peroxyacid therein. The presence of persalts in the wash can supplement avox levels, for example by amounts of from 10 to 100 ppm avox. In use, depending upon whether and the extent to which alkaline materials, especially builders, are present in the composition itself or in any accompanying washing composition, the compositions generate upon dissolution either a mildly acidic through to especially a mildly alkaline pH. It is preferred to generate a pH of from 7.5 to 9.5 and especially around pH of 8 to about 9.0 to optimise bleaching/washing performance from the peroxyacid.

For use in disinfection, it is often preferable to employ an invention peroxyacid concentration of up to 200 ppm avox and in many instances from 25 to 100 ppm avox. It is also suitable to employ a solution spanning neutrality, from mildly acidic, such as at least pH 4 up to mildly alkaline, such as pH 9. In order to attain a pH in such a range, the choice of builders/diluents is so made as to avoid highly alkaline materials and instead select those that generate mild acidity or alkaninity such as sodium dihydrogen phosphate.

The washing processes for laundry can be carried out in currently available equipment. Washing times typically range from about 10 minutes to 30 minutes. Hand washing and extended steeping using solutions of the invention compositions can alternatively or additionally be used. Specialist variations of the invention compositions, such as those intended for nappy sanitisation/cleansing or for denture cleansing are preferably used in the accepted manner for prior art compositions, for example steeping a soiled nappy in a warm peracid-containing solution for several hours before washing it using laundry techniques.

Having described the invention in general terms, specific embodiments will now be described more fully by way of example only.

EXAMPLES 1 AND 2

Preparation of Imido Peroxyacids

In each Example and Comparison, the reaction equation for the acid catalysed reaction was

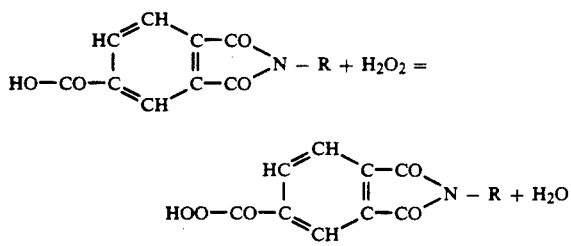

The general preparative route adopted for the first preparation of each peroxyacid was as follows:

N-alkyl imido trimellitic acid starting materials were prepared by condensing trimellitic anhydride with the appropriate n-alkylamine. The subsequent peroxidation is exemplified for n-butylamine-substituted trimellitimide. The results from IR and NMR analyses confirmed the presence of a condensed aromatic imide and carboxylic acid moieties, and acid titration confirmed that there was only one acid group per molecule.

A weighed amount of butylimidotrimellitic acid (BITA) (10 g) was introduced into stirred methanesulphonic acid (70 mls) in a beaker, forming a solution at room temperature, approximately 22°/23° C. in the safety cabinet. Hydrogen peroxide assaying 85% w/w approx. aqueous solution, was pumped via a peristaltic pump with continued stirring into the reaction mixture progressively during a period of about 5 to 10 minutes at a rate controlled so that the mixture's temperature did not rise above 25° C., until a total amount of 4.5 moles per mole of carboxylic acid had been introduced, i.e. a 3.5 molar excess compared with the stoichiometric amount. The reaction mixture was then kept at room temperature for a further 3 hours. At the end of the reaction a substantial fraction of the carboxylic acid had been oxidised to the corresponding peroxycarboxylic acid, which precipitated out of solution and the mixture cooled to below about 5° C. in an ice bath.

The reaction mixture was poured into about 3 times as much iced water per volume of reaction mixture, filtered and the filter cake washed a substantial volume of ice cold water, until the wash water was above pH3, and below pH5 and the filter cake was then air-dried.

The yield of solid was 9.5g having an avox content of 5.64 which indicates a purity of 93% (theoretical avox 6.06%) and a "melting point of 64°-65° C. The peroxyacid product was butyl imido peroxytrimellitic acid, BIPTA.

The avox was measured by a standard technique in which a measured weight of sample was dissolved in acetic acid, if necessary augmented with dichloromethane to ensure that the sample is completely dissolved. The sample is then contacted with a measured amount of sodium carbonate stabilised sodium iodide, in the presence of ferric chloride, allowed to react for 10 minutes in the dark, and the resultant solution is titrated against standardised sodium thiosulphate solution until the pale yellow coloured solution becomes colourless. The result is compared with a corresponding titration against a blank solution, and from the difference the avox is calculated.

All the isolated peroxyacid products were analysed by conventional IR and BIPTA also by NMR techniques to confirm the presence of imido and percarboxylic acid groups in the product molecule.

For the products produced by the route of of Ex 1, e.g. BIPTA, HIPTA etc in the infra-red trace, a shoulder/peak was observed with its centre at 1770 cm$^{-1}$, and a sharp peak at 1705 cm$^{-1}$, which corresponds to a five membered imide ring. A further peak was observed with a centre at about 1720 cm$^{-1}$, indicative of carbonyl stretching in a peroxycarboxylic acid which is a substituent of an aromatic nucleus. There was some tendency for the two latter peaks to merge. It was also observed for both products that there was a substantial absence of peaks at about 3360 cm$^{-1}$, or in the regions of indicated the presence of an amide group obtained by opening of the imide ring during the peroxidation reaction. The spectra for the corresponding imidocarboxylic acid starting materials contained two significant peaks, a peak or shoulder at 1770 cm$^{-1}$ and a broad peak at about 1705 cm$^{-1}$, which correspond to the two peaks for the imide structure, but the second one tending to merge with a similarly located carboxylic acid peak. Thus, from the IR data, it can be deduced that the product retained its alkyltrimellitimido structure and gained a percarboxylic acid group.

NMR analysis
BIPTA was analysed by proton NMR. The chemical shifts and the attributions are given below

| Chemical Shift | Integration | Attribution |
|---|---|---|
| 0.95 | triplet | 3 | CH$_3$ |
| 1.4 | sextuplet | 2 | CH$_2$ |
| 1.7 | pentuplet | 2 | CH$_2$ |
| 3.7 | triplet | 2 | CH$_2$ |
| 7.95 } 8.4 | multiplet | 3 | Aromatic H ($\times$ 3) |

It will be seen that the NMR confirms the presence of a N-butyl group and 3 aromatic C-H groups.

EXAMPLES 2a-i

In these Examples, the route of Example 1 was followed, employing the appropriate other N-alkyl trimellitic acid as starting material. The description of R, the % purity (ratio of measured to theoretical avox), % yield (based on carboxylic acid), and melting point of the product peroxyacid are summarised in Table 1 below.

TABLE 1

| Ex No | Name | R = | % purity | % yield | MP °C. |
|---|---|---|---|---|---|
| 2a | HIPTA | n-heptyl | 96 | 88 | 80 |
| 2b | PrIPTA | n-propyl | 96 | 90 | 97 |
| 2c | PIPTA | n-pentyl | 95 | 94 | 73 |
| 2d | SIPTA | n-hexyl | 92 | 91 | 64 |
| 2e | IPTA | H | 99 | 42 | 175 |
| 2f | MIPTA | methyl | 92 | 69 | 128 |
| 2g | EIPTA | ethyl | 98 | 62 | 120 |
| 2h | iPrIPTA | isopropyl | 90 | 86 | 132-134 |
| 2i | sBIPTA | sec-butyl | 96 | 91 | 91 |

EXAMPLE 3

Alternative Preparation of BIPTA

In this Example, a solution of Caro's acid was prepared by mixing sulphuric acid (98% w/w, 18.2 g) and hydrogen peroxide solution (85% w/w, 2.83 g) and demineralised water (2.36 g) with cooling to 12° C. A solution of BITA (5 g) in sulphuric acid (98% w/w,15 g) was added dropwise in the Caro's acid solution at a reaction temperature maintained at about 35° C., over about 5 minutes with stirring and the reaction continued for a further 75 minutes. The reaction mixture was then quenched by slow addition of ice/water (100 g), filtered and washed as in Example 1. The yield of product was 4.3 g having an avox of 4.56% avox and a purity of about 75%.

EXAMPLES 3a TO 3d

Example 3 was repeated in a modified form, employing the carboxylic acids ITA, PrITA, sBITA and PITA (5 g) as a particulate feed instead of the sulphuric acid solution of BITA. A Caro's acid solution was made from sulphuric acid (98% w/w, 23.1 g), hydrogen peroxide solution (85% w/w, 5.7 g) and demineralised water (1.2 g) at a temperature below 15° C. The carboxylic acids were introduced gradually with stirring into the Caro's acid solution maintained at about 40° C. and the reaction continued for 40 minutes. The mixture was cooled in an ice-bath to about 10° C. and quenched by slow addition of ice/water, filtered and washed to pH3. The purity of the products isolated were respectively 95.5%, 90%, 91.6% and 84.4%.

Comparison Aromatic Imido Peroxyacid

Phthalimido-2-peroxyacetic acid (TIP2), a compound according to Example 1 of EP-A-0 325 289, was made in a similar process to that employed for Example 1 herein from commercially available phthalimido-2-acetic acid.

Peroxyacid Performance

The peroxyacids were subjected to a number of tests to determine their effectiveness as a bleach, their hazard rating and their storage stability. The compound were also compared in these tests with a reference peroxyacid, diperoxydodecanedioc acid, DPDDA, a peroxyacid that has emerged during the last eight years as a favourite organic peroxide amongst washing composition manufacturers like Procter & Gamble.

The tests were carried out as follows:

Storage stability

In this test, weighed samples of the peroxyacid are individually sealed in glass phials with a bubbler cap that permits excess internal pressure to vent to atmosphere, and stored in a dark chamber that is thermostatically controlled to 32° C. The avox of the peroxyacid is measured shortly after its preparation i.e. $A_0$ and after predetermined storage intervals, $A_s$, the measurement being made on entire individual samples. The stability results of stored samples are $A_s/A_0$, quoted as a percentage, the higher the better.

Avox is measured using the same method as described hereinabove.

It will be recognized that the storage stability of the peroxyacid by itself is an extremely important characteristic of a peroxyacid, not only because the compound is likely to be stored in that way before it is encorporated in specific compositions, but also because it represents the intrinsic stability of the compound, the maximum attainable even if the remaining components of compositions containing it are benign.

A + indicates that the compound is according to the invention whereas a — indicates that it is present by way of comparison.

TABLE 2

| Compound | Proportion of avox remaining after | | |
|---|---|---|---|
| | 1 week | 4 weeks | longest/n weeks |
| +IPTA | 100 | 95 | 97/8 w |
| +MIPTA | 97 | 98 | 98/8 w |
| +EIPTA | 99 | 97 | 97/8 w |
| +PrIPTA | 100 | 99 | 99/8 w |
| +BIPTA | 97 | 81 | |
| +sBIPTA | 94 | 96 | 95/8 w |
| +PIPTA | 99 | 100 | 98/12 w |
| +SIPTA | 100 | 94 | 90/12 w |
| +HIPTA | 100 | 95 | 95/12 w |
| −TIP2 | 100 | 87 | 13/16 w |
| −DPDDA | 97 | 85 | |

This Table demonstrates that the storage stability of imidoaromatic peroxyacids depends very greatly upon the nature and disposition of the substituents, and that the comparison peroxyacid, TIP2, is markedly inferior. The invention peroxyacid containing the sec-butyl, pentyl or heptyl substituent showed truly outstanding stabilisation.

Hazard Rating

Two tests are described below to demonstrate the hazard rating of the peroxyacid. They are respectively an impact sensitivity test and a pressure-time test.

In the impact sensitivity test, a weight (in kg) is dropped once from a measured height (in cm) onto a fresh sample of the peroxyacid held in the anvil. The sample is thus subjected to an impact, normally expressed as kg-cm (1 kg-cm = $9.8 \times 10^{-2}$J) that is proportionate to the height and weight. The test is carried out many times at each impact strength, and is observed to see whether the sample responds, by charring, emitting smoke or at worst undergoing a minor explosion. The tests start at a low impact strength and are continued at increasing strengths until the limiting result is obtained, being the earlier of either 50% of the tests at that impact strength give positive results or a figure of 500 kg-cm is reached, which past experience indicates to represent a non-impact-sensitive product. The limiting result in kg-cm is shown in Tables summarising the results, the higher the better.

In the pressure-time test, 2 g samples of the test material is placed inside an 18 ml steel bomb, and its decomposition initiated. The consequential rise in pressure is monitored and plotted or displayed against elapsed time, expressed in milliseconds. In Table 3, the time is given for the pressure in the bomb generated by the sample to increase from 100 to 300 psi, i.e. from $6.895 \times 10^5$ Pa to $2.068 \times 10^6$ Pa, the longer the better. The symbol ∞ indicates that a pressure of 300 psi was not reached, i.e. a period of infinite duration. By way of interpretation, a time of less than 30 milliseconds indicates that the material is potentially explosive, a time of 30 to 60 milliseconds indicates that it is marginally explosive, and to allow a safety margin, it is preferred to be around 100 milliseconds or longer.

TABLE 3

| Compound | Hazards rating results | |
|---|---|---|
| | Impact kg-cm | p-t msec |
| +BIPTA | >500 | ∞ |
| +HIPTA | >500 | ∞ |
| −TIP2 | 75 | 30 |

TABLE 3-continued

| Compound | Hazards rating results | |
|---|---|---|
| | Impact kg-cm | p-t msec |
| −DPDDA | >500 | 30 |

Trials on IPTA, MIPTA, EIPTA, PrIPTA, sBIPTA, PIPTA, and SIPTA gave the same result as for BIPTA, except that a sample of IPTA (made in Example 3a) gave a p-t of 120 msec.

From Table 3, it can be seen that the invention imidoperoxyacids were all much safer, as demonstrated by the impact test than the comparison imido peroxyacid TIP2, and in the pressure-time test, were significantly safer than the reference compound DPDDA as well as TIP2. These tests show that the selection of suitable substituents in aromatic imido peroxyacid compounds is of crucial significance in order to obtain a product that is inherently safe to handle.

Bleach/washing evaluation

The effectiveness of the invention and comparison peroxyacids was tested by washing swatches of cotton cloth that had been preimpregnated in a standard manner with one of four representative stains, tea, red wine, grass and blue polish. The evaluations were carried out in a laboratory scale washing machine, a "Tergotometer" (Trade Mark) available from the US Testing Corporation, under identical standardised conditions. The washing solution comprised local Cheshire tap water, hardness of about 160 to 180 ppm hardness as calcium carbonate, in which was dissolved a peroxyacid-free washing composition at 6.5 g/l. Composition NSPA used in all trials had the approximate analysis:

| Composition Component | NSPA % w/w |
|---|---|
| Anionic surfactant | 9 |
| Nonionic surfactant | 8 |
| Other organics | 1 |
| Sodium carbonate | 3 |
| Sodium sulphate | 19 |
| Sodium phosphate | 36 |
| Sodium silicate | 10 |
| Sodium Borate | 4 |
| Water | balance |

A weighed amount of peroxyacid was introduced into the washing solution to provide a peracid avox of 25 ppm therein, assuming total dissolution. This corresponds to a molar concentration of $1.56 \times 10^{-3}$M monoperoxyacid. The washing solution was kept at pH9 and at 40° C. during the washing period of 20 minutes. The swatches were then rinsed and dried and the extent of stain removal was determined by comparing the reflectance of the washed cloth, $R_w$, with that of the pre-washed, stained cloth, $R_s$, and that of the unstained cloth, $R_u$. The measurements were obtained using an Instrumental Colour System "Micromatch" (Trade Mark) reflectance spectrophotometer equipped with a Xenon lamp filtered through a D65 conversion filter to approximate to CIE artificial daylight Stain Removal, expressed a s percentage, was calculated using the formula:

$$\%SR = 100 \times [R_w - R_s]/[R_u - R_s]$$

It will be recognised that by demonstrating the washing capability of the peroxyacids in this way, the tests using the invention peroxyacids are in themselves Examples of washing processes according to other aspects of the present invention. Similarly, since the swatches had not been stored in sterile conditions before being washed, the washing procedure will act simultaneously to disinfect them.

The results quoted below are the mean of two evaluations. Comparative results on the same stained cloths using the washing composition by itself, i.e. without any added peracid, are designated "base".

TABLE 4

| Ex/Comp No | Peracid employed | % Stain Removal | | | | |
|---|---|---|---|---|---|---|
| | | Red Wine | Grass | Tea | Blue Polish | Average Removal |
| C4 | base | 78 | 78 | 46 | 58 | 65 |
| 5 | BIPTA | 95 | 97 | 77 | 74 | 86 |
| 6 | HIPTA | 90 | 89 | 59 | 72 | 80 |
| C6 | DPDDA | 91 | 94 | 74 | 61 | 80 |

From Table 4, it can be seen that the invention peracid are very effective bleaching agent at hand-hot washing temperatures, not only by comparison with a peracid-free base composition, but showing very similar or superior effectiveness overall compared with DPDDA, although with a distinct bias towards the more hydrophobic stains. The trials demonstrate in particular that the shorter alkyl substituted imido compound, BIPTA has especially attractive washing performance and that the invention compounds as a class perform particularly well against hydrophobic stains.

A repeat set of washing trials were also carried under the same washing conditions, employing the same base washing composition at the same concentration, and further samples of the four stains, to compare the effectiveness of the N-n propyl- compound (PrIPTA), with DPDDA (each providing 25 ppm avox) and base composition alone. The average stain removal was 64% for the base alone, 80% for DPDDA and over 81% for PrIPTA. This confirms that PrIPTA is a particularly effective bleaching agent over a range of domestic stains.

Further repeat sets of washing trials were conducted using the same conditions as respectively comparisons C4 and C6 and Example 5, using the peroxyacids specified in Table 4A below.

TABLE 4A

| Ex/Comp No | Peracid employed | % Stain Removal | | | | |
|---|---|---|---|---|---|---|
| | | Red Wine | Grass | Tea | Blue Polish | Average Removal |
| C4A | base | 73 | 78 | 59 | 49 | 65 |
| E4i | IPTA | 94 | 87 | 81 | 57 | 80 |
| C4B | base | 74 | 76 | 54 | 53 | 64 |
| C4C | DPDDA | 91 | 90 | 79 | 66 | 82 |
| E4ii | MIPTA | 90 | 87 | 83 | 51 | 78 |
| E4iii | EIPTA | 95 | 93 | 79 | 58 | 81 |
| E4iv | PrIPTA | 93 | 94 | 82 | 64 | 83 |
| E4v | PIPTA | 94 | 97 | 79 | 74 | 86 |
| E4vi | SIPTA | 93 | 98 | 79 | 80 | 88 |
| C4D | base | 78 | 78 | 46 | 58 | 65 |
| C4E | DPDDA | 91 | 94 | 74 | 61 | 80 |
| E4vii | iPrIPTA | 96 | 93 | 80 | 73 | 86 |
| E4viii | sBIPTA | 95 | 96 | 80 | 67 | 88 |

From Table 4A, it can be seen that the invention peroxyacids tested in Examples E4i through to E4viii performed substantially better than the base washing composition alone, and that a number of the peroxyacids, including specifically PrIPTA, PIPTA, SIPTA, iPrIPTA and sBIPTA are seen to be especially effective washing/bleaching compounds by virtue of the fact that they out-perform DPDDA.

Formulations

Representative formulations are made by dry mixing particulate invention peroxyacid with a premixture of the remaining components of compositions intended for particular uses which are specified in the respective following Tables. In the formulations, iPrIPTA (tq) contains 90% w/w active peroxyacid and has a measured avox of 5.7% w/w; sBIPTA (tq) contains 96% w/w active peroxyacid and has a measured avox of 5.7% w/w; PIPTA (tq) contains 94% w/w active peroxyacid and has a measured avox of 5.4% w/w; SIPTA (tq) contains 92% w/w active peroxyacid and has a measured avox of 5.0% w/w; BIPTA (tq1) contains 73% w/w active peroxyacid and has a measured avox of 4.4% w/w; BIPTA (tq2) contains 96% w/w active peroxyacid and has a measured avox of 5.8% w/w; HIPTA (tq) contains 86% w/w active peroxyacid and has a measured avox of 4.5% w/w. LAS represents a linear alkyl benzene sulphonate, sodium salt, average alkyl length of C11.5, and OBA represents an optical brightening agent. Similar formulations, i.e. capable of delivering the same number of moles of peroxyacid as the representative formulations are obtained by substituting the calculated proportion of the replacement peroxyacid for that shown, using the ratio of the known avox contents of the two peroxyacids, and correspondingly adjusting the content of the filler or bulking agent that is normally employed in the formulations, such as sodium sulphate or sodium chloride.

EXAMPLES 7 TO 9A

Bleach Additive Formulations are obtained by dry blending the particulate components specified in Table 5.

TABLE 5

| Example No Components | 7 % w/w | 7A % w/w | 8 % w/w | 8A % w/w | 9 % w/w | 9A % w/w |
|---|---|---|---|---|---|---|
| BIPTA (tq1) | 9.2 | | | | | |
| BIPTA (tq2) | | | 27.6 | | | |
| sBIPTA (tq) | | 7.0 | | | | |
| PIPTA (tq) | | | | 29.7 | | |
| SIPTA (tq) | | | | | | 63.8 |
| HIPTA (tq) | | | | | 71.1 | |
| LAS | 3 | 3 | 4 | 4 | 5 | 5 |
| OBA + chelate | 0.2 | 0.2 | 0.2 | 0.2 | 0.2 | 0.2 |
| Sodium sulphate | 87.6 | 89.8 | 68.2 | 66.1 | 23.7 | 31.0 |

Dosing of formulations at 1.25 gpl provides respectively approximate avox concentrations in solution of 5 ppm for 7 and 7A, 20 ppm for 8 and 8A, and 40 ppm for 9 and 9A. Solid bleach additive compositions containing a pH buffer to lower the solution pH closer to about pH 8.5, and hence improve stain removal are made by replacing about 10% w/w of the sodium sulphate by boric acid.

EXAMPLES 10 TO 15

Representative washing compositions according to the present invention are made by dry mixing the particulate invention peroxyacid with a blend of the other components shown in Table 6. The abbreviations STPP and PBS1 represent respectively sodium tripolyphosphate and sodium perborate monohydrate. The chelate is EDTMP, ethylene diamino (tetramethylene phosphonate), Na salt or CDTMP, cyclohexane diamino(tetramethylene phosphonic acid).

Use of Example formulations 10 to 15 at a concentration of 8 gpl in the washing liquor, a typical level for front loading washing machines in Europe, results in peracid avox concentrations of approximately 10, 20, 30, 15, 25, and 35 ppm respectively.

TABLE 6

| Example No Components | 10 % w/w | 11 % w/w | 12 % w/w | 13 % w/w | 14 % w/w | 15 % w/w |
|---|---|---|---|---|---|---|
| BIPTA (tq1) | 2.9 | | | | | |
| HIPTA (tq) | | 5.6 | | | | |
| BIPTA (tq2) | | | 6.5 | | | |
| sBIPTA (tq) | | | | 3.3 | | |
| PIPTA (tq) | | | | | 5.8 | |
| SIPTA (tq) | | | | | | 8.8 |
| LAS | 7.0 | 9.6 | 8.6 | 7.0 | 6.0 | 6.0 |
| Alcohol Ethoxylate | 5.1 | 3.8 | 5.7 | 2.5 | 6.0 | 7.0 |
| STPP | 34.0 | 26.1 | | 40.0 | 30.0 | 30.0 |
| Zeolite A | | | 22.5 | | | |
| Carboxylate builder | | 2.0 | 15.0 | | | |
| Sodium sulphate | 13.8 | 36.8 | 24.8 | 18.8 | 24.2 | 16.4 |
| Sodium silicate | 14.0 | 6.7 | 7.6 | 6.5 | 5.0 | 5.0 |
| Soap | 6.5 | | | 3.0 | 3.0 | 2.0 |
| Buffer (boric acid) | 10.0 | | | 10.0 | 10.0 | 10.0 |
| PBS1 | | | | | | 9.0 |
| CMC | 1.0 | 1.0 | 1.0 | 1.0 | 1.0 | 1.0 |
| Minors (Chelate + OBA + Perfume etc) | 0.4 | 0.4 | 0.4 | 0.6 | 0.3 | 0.5 |
| Water | | | balance | | | |

EXAMPLES 16 TO 18A

Representative Sanitizer Formulations are made by dry mixing the specified invention peroxyacids with the other particulate components specified in Table 7.

When these formulations are dosed into a nappy (or similar article) sanitising solution in an amount of 5 gpl, the invention peroxyacids provide an approximate avox of respectively 15 ppm for 16, 16A, 25 ppm for 17, 17A and 35 ppm for 18, 18A.

TABLE 7

| Components % w/w | 16 | 16A | 17 | 17A | 18 | 18A |
|---|---|---|---|---|---|---|
| BIPTA (tq1) | 6.8 | | | | | |
| HIPTA (tq) | | | 11.1 | | | |
| iPrITA (tq) | | 5.3 | | | | |
| sBIPTA (tq) | | | | 8.8 | | |
| PIPTA (tq) | | | | | 13.0 | |
| SIPTA (tq) | | | | | | 14.0 |
| LAS | 9.0 | 9.0 | 7.0 | 7.0 | 5.0 | 5.0 |
| Sodium carbonate | 20.0 | 20.0 | 23.0 | 23.0 | | |
| STPP | 10.0 | 10.0 | 10.0 | 10.0 | 10.0 | 10.0 |
| Sodium bicarbonate | | | | | 26.0 | 26.0 |
| Sodium chloride | 45.7 | 47.2 | 47.2 | 49.5 | 45.2 | 44.2 |
| Borax | 8.5 | 8.5 | | | | |
| Organic chelate | | | 1.2 | 1.2 | 0.8 | 0.8 |

EXAMPLES 19 TO 21A

Particulate dilute disinfectant compositions are made by dry mixing the components specified in Table 8.

TABLE 8

| Components % w/w | 19 | 19A | 20 | 20A | 21 | 21A |
|---|---|---|---|---|---|---|
| BIPTA (tq1) | 6.8 | | | | | |
| HIPTA (tq) | | | 11.3 | | | |
| iPrITA (tq) | | 5.3 | | | | |
| BIPTA (tq2) | | | | | 12.1 | |
| PIPTA (tq) | | | | 9.4 | | |
| SIPTA (tq) | | | | | | 14.0 |

TABLE 8-continued

| Components % w/w | Example No | | | | | |
|---|---|---|---|---|---|---|
| | 19 | 19A | 20 | 20A | 21 | 21A |
| Sodium dihydrogen phosphate | 10.0 | 10.0 | 10.0 | 10.0 | 10.0 | 10.0 |
| Boric acid | 5.0 | 5.0 | 5.0 | 5.0 | 5.0 | 5.0 |
| Corrosion Inhibitor | 1.0 | 1.0 | 1.0 | 1.0 | 1.0 | 1.0 |
| Perfume | 0.5 | 0.5 | 0.5 | 0.5 | 0.5 | 0.5 |
| Sodium sulphate | 76.7 | 78.2 | 72.2 | 74.1 | 71.4 | 69.5 |

When these formulations are employed at a dose level of 1 glp in an aqueous medium requiring disinfection, the approximate concentration of avox therein is respectively 3 ppm for 19, 19A, 5 ppm for 20, 20A and 7 ppm for 21, 21A.

EXAMPLES 22 TO 24

Disintegrating Tablet compositions, suitable for dentures are made by dry mixing the components given in Table 9 below, and then subjecting them to compression in the mould of a tabletting machine to make tablet weighing about 4 g. The polyethyleneglycol binder av mol weight 6000 is designated PEG 6000, the disintegrant was a cross linked polyvinylpyrrolidone available under the Trademark POLYPLASDONE XL and the lubricant was sodium lauryl sulphate.

TABLE 9

| Example No | 22 | 23 | 24 |
|---|---|---|---|
| Particulate Components | % w/w | % w/w | % w/w |
| BIPTA (tq1) | 9.7 | | |
| HIPTA (tq) | | 11.9 | |
| PIPTA (tq) | | | 11.6 |
| Succinic acid | 25.2 | 15.0 | 15.0 |
| Sodium Bicarbonate | | 25.5 | 40.0 |
| Sodium Carbonate | 10.0 | | |
| PEG 6000 (binder) | 6.0 | 6.0 | 6.0 |
| PVP disintegrant | 1.0 | 1.0 | 1.0 |
| Lubricant | 0.2 | 0.2 | 0.2 |
| Sodium sulphate | 47.9 | 40.4 | 26.0 |

When one tablet of composition 22, 23 or 24 is introduced into water it generates respectively 17, 21.5 or 25 mg avox.

We claim:

1. An organic peroxyacid which satisfies formula (1):

$$\text{R-N} \begin{matrix} \diagup \text{CO-C} \\ \diagdown \text{CO-C} \end{matrix} \begin{matrix} \diagdown \text{C} \diagup \\ \| \\ \diagup \text{C} \diagdown \end{matrix} \begin{matrix} \text{C-CO-OOH} \\ \| \end{matrix} \quad (I)$$

in which R represents hydrogen or a low molecular weight alkyl group containing up to 8 linear carbon atoms.

2. A peroxyacid according to claim 1 in which R represents a linear n-alkyl or branched alkyl group containing from 3 to 7 carbon atoms.

3. A peroxyacid according to claim 1 in which R represents hydrogen, propyl, iso-propyl, butyl, iso-butyl, sec-butyl, pentyl or hexyl.

4. A bleach composition containing from 1 to 80% w/w of an organic peroxyacid which satisfies the formula (1):

$$\text{R-N} \begin{matrix} \diagup \text{CO-C} \\ \diagdown \text{CO-C} \end{matrix} \begin{matrix} \diagdown \text{C} \diagup \\ \| \\ \diagup \text{C} \diagdown \end{matrix} \begin{matrix} \text{C-CO-OOH} \\ \| \end{matrix} \quad (I)$$

in which R represents hydrogen or a low molecular weight alkyl group containing up to 8 linear carbon atoms and from 99 to 20% w/w of a diluent.

5. A washing composition containing from 0.5 to 50% w/w of an organic peroxyacid which satisfies the formula (1)

$$\text{R-N} \begin{matrix} \diagup \text{CO-C} \\ \diagdown \text{CO-C} \end{matrix} \begin{matrix} \diagdown \text{C} \diagup \\ \| \\ \diagup \text{C} \diagdown \end{matrix} \begin{matrix} \text{C-CO-OOH} \\ \| \end{matrix} \quad (I)$$

in which R represents hydrogen or a low molecular weight alkyl group containing up to 8 linear carbon atoms, from 1 to 90% surfactant, from 0 to 90% detergent builder, from 0 to 99% diluent and from 0 to 20% auxilliary agents.

6. In a method of bleaching in which an item to be bleached is contacted with an effective amount of a bleaching agent, the improvement wherein the bleaching agent comprises a peroxyacid which satisfies the formula:

$$\text{R-N} \begin{matrix} \diagup \text{CO-C} \\ \diagdown \text{CO-C} \end{matrix} \begin{matrix} \diagdown \text{C} \diagup \\ \| \\ \diagup \text{C} \diagdown \end{matrix} \begin{matrix} \text{C-CO-OOH} \\ \| \end{matrix}$$

in which R represents hydrogen or a low molecular weight alkyl group containing up to 8 linear carbon atoms.

7. A method according to claim 6 wherein R represents a linear n-alkyl or branched alkyl group containing from 3 to 7 carbon atoms.

8. A method according to claim 6 wherein R represents hydrogen, propyl, iso-propyl, butyl, iso-butyl, sec-butyl, pentyl or hexyl.

9. A method according to claim 6 wherein said bleaching agent is provided in a bleaching composition which further comprises from 99 to 20% w/w of a diluent.

10. In a method of disinfecting in which an item to be disinfected is contacted with an effective amount of a disinfecting agent, the improvement wherein the disinfecting agent comprises a peroxyacid which satisfies the formula:

$$\text{R-N} \begin{matrix} \diagup \text{CO-C} \\ \diagdown \text{CO-C} \end{matrix} \begin{matrix} \diagdown \text{C} \diagup \\ \| \\ \diagup \text{C} \diagdown \end{matrix} \begin{matrix} \text{C-CO-OOH} \\ \| \end{matrix}$$

in which R represents hydrogen or a low molecular weight alkyl group containing up to 8 linear carbon atoms.

11. A method according to claim 10 wherein R represents a linear n-alkyl or branched alkyl group containing from 3 to 7 carbon atoms.

12. A method according to claim 10 wherein R represents hydrogen, propyl, iso-propyl, butyl, iso-butyl, sec-butyl, pentyl or hexyl.

13. A method according to claim 6 wherein said disinfecting agent is provided in a disinfecting composition which further comprises from 99 to 20% w/w of a diluent.

14. A method of washing in which an item to be washed is contacted with an effective amount of a washing agent, the improvement wherein the washing agent comprises a peroxyacid which satisfies the formula:

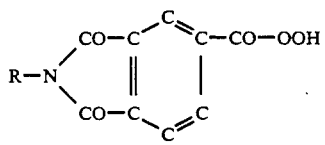

in which R represents hydrogen or a low molecular weight alkyl group containing up to 8 linear carbon atoms.

15. A method according to claim 14 wherein R represents a linear n-alkyl or branched alkyl group containing from 3 to 7 carbon atoms.

16. A method according to claim 14 wherein R represents hydrogen, propyl, iso-propyl, butyl, iso-butyl, sec-butyl, pentyl or hexyl.

17. A method according to claim 14 wherein said washing agent is provided in a disinfecting composition which further comprises from 1 to 90% surfactant, from 0 to 90% detergent builder, from 0 to 90% diluent, and from 0 to 20% auxilliary agents.

* * * * *